United States Patent [19]
Jeannin

[11] Patent Number: 6,096,329
[45] Date of Patent: *Aug. 1, 2000

[54] INSECTICIDAL COMBINATION TO CONTROL MAMMAL FLEAS, IN PARTICULAR FLEAS ON CATS AND DOGS

[75] Inventor: Philippe Jeannin, Tournefeuille, France

[73] Assignee: Merial, Lyons, France

[*] Notice: This patent issued on a continued prosecution application filed under 37 CFR 1.53(d), and is subject to the twenty year patent term provisions of 35 U.S.C. 154(a)(2).

[21] Appl. No.: 08/863,692

[22] Filed: May 27, 1997

Related U.S. Application Data

[63] Continuation-in-part of application No. 08/692,113, Aug. 5, 1996, abandoned.

[30] Foreign Application Priority Data

Mar. 29, 1996 [FR] France ................................. 96 04208
Mar. 26, 1997 [FR] France ................................. 97 03711

[51] Int. Cl.⁷ ........................... A01N 43/56; A01N 43/40
[52] U.S. Cl. ........................... 424/405; 514/407; 514/875
[58] Field of Search ........................... 424/405; 514/875, 514/407

[56] References Cited

U.S. PATENT DOCUMENTS 5,516,787  5/1996  Takada .
5,567,429  10/1996 Senbo .
5,629,334  5/1997  Takada .

FOREIGN PATENT DOCUMENTS

WO 98/25466  6/1998  WIPO .

*Primary Examiner*—S. Mark Clardy
*Attorney, Agent, or Firm*—Frommer Lawerence & Haug, LLP; William S. Frommer; Thomas J. Kowalski

[57] ABSTRACT

Process and composition, in particular for controlling fleas on small mammals, characterized in that the composition includes, on the one hand, at least one insecticide of 1-N-arylpyrazole type, in particular fipronil, and, on the other hand, at least one compound of IGR (insect growth regulator) type, in doses and proportions which are parasiticidally effective on fleas, in a fluid vehicle which is acceptable for the animal and convenient for local application to the skin, preferably localized over a small surface area.

70 Claims, No Drawings

INSECTICIDAL COMBINATION TO CONTROL MAMMAL FLEAS, IN PARTICULAR FLEAS ON CATS AND DOGS

This application has been filed as a continuation-in-part of Ser. No.08/692,113 filed Aug. 5, 1996, now abandoned.

The present invention relates to an improvement to the processes for controlling mammal fleas and in particular fleas on cats and dogs. The invention also relates to a novel composition for this use, based on a synergistic combination of parasiticides which are already known. Lastly, the invention relates to the use of such already-known parasiticides for the preparation of such a composition.

A novel class of 1-N-arylpyrazole-based insecticides has been described in patents EP-A-295,217 and EP-A-352,944. The compounds of the classes defined in these patents are highly active, and one of these compounds 1-[2,6-Cl$_2$ 4-CF$_3$ phenyl]3-CN 4-[SO—CF$_3$]5-NH$_2$ pyrazole, whose common name is fipronil, has proven to be particularly effective not only against crop parasites but also against mammal ectoparasites and in particular, but not exclusively, fleas, ticks, flies and myiases.

Compounds with an ovicidal and/or larvicidal effect on the immature stages of various ectoparasites are already known, for example from patent U.S. Pat. No. 5,439,924. Among these compounds are featured insect growth regulator compounds (IGR) which act either by blocking the development of the immature stages (eggs and larvae) into adult stages, or by inhibiting the synthesis of chitin.

Patent FR-A-2,713,889 is moreover known, which generally describes the combination of at least one compound of IGR (insect growth regulator) type, comprising compounds with juvenile hormone activity and chitin synthesis inhibitors, with at least one of three N-aryldiazole compounds, in particular fipronil, to control many harmful insects belonging to very varied orders.

The compositions may be used in very diverse forms, although the applications, for example veterinary, healthcare or plant-protection applications, for which these different forms are designed are not specified, nor are the parasites for which they are respectively intended.

The only application which may be thought to be veterinary is associated with the example of the manufacture of a pesticidal collar which is a slow-release formulation.

The invention proposes to improve the processes for controlling fleas in small mammals, and in particular in cats and dogs.

The object of the invention is, in particular, to use already-known parasiticides in order to prepare a composition which is highly active against the fleas of these animals.

Lastly, the object of the invention is a novel composition thus prepared and intended, in particular, to control fleas.

For the purposes of the present invention, the term flea is understood to refer to all the usual or accidental species of parasitic flea of the order Siphonaptera, and in particular the species Ctenocephalides, in particular *C. felis* and *C. canis*, rat fleas (*Xenopsylla cheopis*) and human fleas (*Pulex irritans*).

The very high efficacy of the process and of the composition according to the invention implies not only high immediate efficacy but also very long-lasting efficacy after the animal has been treated.

The subject of the invention is a process for controlling the fleas of small mammals, and in particular cats and dogs, over a long period, characterized in that the animal is treated by locally depositing on the skin, preferably localized over a small surface area (spot-on application), in parasiticidally effective doses and proportions, on the one hand at least one compound (A) belonging to formula (I),

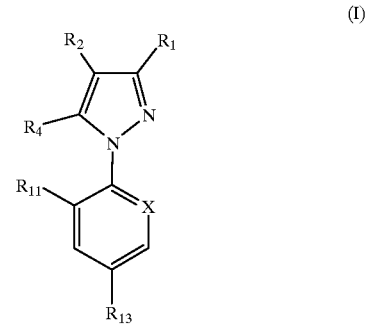

in which:
R$_1$ is CN or methyl or a halogen atom;
R$_2$ is S(O)$_n$R$_3$ or 4,5-dicyanoimidazol-2-yl or haloalkyl;
R$_3$ is alkyl or haloalkyl;
R$_4$ represents a hydrogen or halogen atom; or a member of a group consisting of NR$_5$R$_6$, S(O)$_m$R$_7$, C(O)R$_7$, C(O) O—R$_7$, alkyl, haloalkyl, OR$_8$ and —N=C(R$_9$) (R$_{10}$);
R$_5$ and R$_6$ independently represent a hydrogen atom or an alkyl, haloalkyl, C(O)alkyl, alkoxycarbonyl or S(O)$_r$—CF$_3$ radical; or R$_5$ and R$_6$ may together form a divalent alkylene radical which may be interrupted by one or two divalent hetero atoms such as oxygen or sulphur;
R$_7$ represents an alkyl or haloalkyl radical;
R$_8$ represents an alkyl or haloalkyl radical or a hydrogen atom;
R$_9$ represents an alkyl radical or a hydrogen atom;
R$_{10}$ represents a phenyl or heteroaryl group optionally substituted with one or more halogen atoms or a member of the group consisting of OH, —O-alkyl, S-alkyl, cyano and alkyl;
R$_{11}$ and R$_{12}$ represent, independently of each other, a hydrogen or halogen atom, or possibly CN or NO$_2$;
R$_{13}$ represents a halogen atom or a haloalkyl, haloalkoxy, S(O)$_q$CF$_3$ or SF$_5$ group;
m, n, q and r represent, independently of each other, an integer equal to 0, 1 or 2
X represents a trivalent nitrogen atom or a radical C—R$_{12}$, the other three valency positions of the carbon atom forming part of the aromatic ring
with the proviso that when R$_1$ is methyl, either R$_3$ is haloalkyl, R$_4$ is NH$_2$, R$_{11}$ is Cl, R$_{13}$ is CF$_3$ and X is N; or R$_2$ is 4,5-dicyanoimidazol-2-yl, R$_4$ is Cl, R$_{11}$ is Cl, R$_{13}$ is CF$_3$ and X is =C—Cl;
and, on the other hand at least one compound (B), of IGR (insect growth regulator) type, in a fluid vehicle which is acceptable for the animal and suitable for local application on the skin.

Preferably, one uses at least one compound (A) belonging to the formula (I) in which:
R$_1$ is CN or methyl
R$_2$ is S(O)$_n$R$_3$
R$_3$ is alkyl or haloalkyl
R$_4$ represents a hydrogen or halogen atom; or a radical NR$_5$R$_6$, S(O)$_m$R$_7$, C(O)R$_7$, alkyl, haloalkyl or OR$_8$ or a radical —N=C(R$_9$) (R$_{10}$)
R$_5$ and R$_6$ independently represent a hydrogen atom or an alkyl, haloalkyl, C(O)alkyl or S(O)$_r$—CF$_3$ radical; or R$_5$ and R$_6$ may together form a divalent alkylene radical which may be interrupted by one or two divalent hetero atoms such as oxygen or sulphur $R_7$ represents an alkyl or haloalkyl radical $R_8$ represents an alkyl or haloalkyl radical or a hydrogen atom $R_9$ represents an alkyl radical or a hydrogen atom $R_{10}$ represents a phenyl or heteroaryl group optionally substituted with one or more halogen atoms or groups such as OH, —O-alkyl, S-alkyl, cyano or alkyl $R_{11}$ and $R_{12}$ represent, independently of each other, a hydrogen or halogen atom $R_{13}$ represents a halogen atom or a haloalkyl, haloalkoxy, $S(O)_q CF_3$ or $SF_5$ group m, n, q and r represent, independently of each other, an integer equal to 0, 1 or 2

X represents a trivalent nitrogen atom or a radical C—$R_{12}$, the other three valency positions of the carbon atom forming part of the aromatic ring with the proviso that when $R_1$ is methyl, then $R_3$ is haloalkyl, $R_4$ is $NH_2$, $R_{11}$ is Cl, $R_{13}$ is $CF_3$ and X is N.

Compounds of formula (I) in which $R_1$ is CN will be selected most particularly. Compounds in which $R_2$ is $S(O)_n R_3$, preferably with n=1, $R_3$ preferably being $CF_3$ or alkyl, for example methyl or ethyl, or alternatively n=0, $R_3$ preferably being $CF_3$, as well as those in which X=C—$R_{12}$, $R_{12}$ being a halogen atom, will also be selected. Compounds in which $R_{11}$ is a halogen atom and those in which $R_{13}$ is haloalkyl, preferably $CF_3$, are also preferred. Within the context of the present invention, compounds which combine two or more of these characteristics will advantageously be selected.

A preferred class of compounds of formula (I) consists of compounds such that $R_1$ is CN, $R_3$ is haloalkyl, $R_4$ is $NH_2$, $R_{11}$ and $R_{12}$ are, independently of each other, a halogen atom, and/or $R_{13}$ is haloalkyl. Preferably also, X is C—$R_{12}$.

In these compounds, $R_3$ preferably represents $CF_3$ or ethyl.

In the present invention, the alkyl radicals may contain generally from 1 to 6 carbon atoms. The ring formed by the divalent alkylene radical representing $R_5$ and $R_6$, as well as the nitrogen atom to which $R_5$ and $R_6$ are attached, may be generally a 5-, 6- or 7-membered ring.

A compound of formula (I) which is most particularly preferred in the invention is 1-[2,6-$Cl_2$ 4-$CF_3$phenyl]3-CN 4-[SO—$CF_3$] 5-$NH_2$ pyrazole, the common name of which is fipronil.

The two compounds which differ from the above by the following characteristics:
1- n=0, $R_3$=$CF_3$
2- n=1, $R_3$=ethyl.
may also be mentioned.

Among the compounds (B), mention may be made in particular of compounds which mimic juvenile hormones, in particular:
azadirachtin—Agridyne
diofenolan (Ciba Geigy)
fenoxycarb (Ciba Geigy)
hydroprene (Sandoz)
kinoprene (Sandoz)
methoprene (Sandoz)
pyriproxyfen (Sumitomo/Mgk)
tetrahydroazadirachtin (Agridyne)
4-chloro-2-(2-chloro-2-methylpropyl)-5-(6-iodo-3-pyridylmethoxy)pyridizin-3(2H)-one
and chitin-synthesis inhibitors, in particular:
chlorfluazuron (Ishihara Sangyo)
cyromazine (Ciba Geigy)
diflubenzuron (Solvay Duphar)
fluazuron (Ciba Geigy)
flucycloxuron (Solvay Duphar)
flufenoxuron (Cyanamid)
hexaflumuron (Dow Elanco)
lufenuron (Ciba Geigy)
tebufenozide (Rohm & Haas)
teflubenzuron (Cyanamid)
triflumuron (Bayer)
these compounds being defined by their international common name (The Pesticide Manual, 10th edition, 1994, Ed. Clive Tomlin, Great Britain).

As chitin-synthesis inhibitors, mention may also be made of compounds such as 1-(2,6-difluorobenzoyl)-3-(2-fluoro-4-(trifluoromethyl)phenylurea, 1-(2,6-difluorobenzoyl)-3-(2-fluoro-4-(1,1,2,2-tetrafluoroethoxy)phenylurea and 1-(2,6-difluorobenzoyl)-3-(2-fluoro-4-trifluoro-methyl)phenylurea.

Novaluron (Isagro, Italian company) may also be mentioned as a compound (B).

The preferred compounds (B) are methoprenes, pyriproxyfens, hydroprene, cyromazine, lufenuron and 1-(2,6-difluorobenzoyl)-3-(2-fluoro-4-(trifluoromethyl)phenylurea.

Another preferred compound (B) is again novaluron.

It is preferable for the administration of the two types of compound to be concomitant and preferably simultaneous.

It is preferable for the treatment according to the invention to be carried out every two or, preferably, every three months on cats and dogs.

Preferably, the treatment is carried out so as to administer to the animal a dose of from 0.1 to 40 and in particular from 1 to 20 mg/kg of derivative (A) and a dose of from 0.1 to 40 and in particular 1 to 30 mg/kg of compound (B).

The preferred doses are from 5 to 15 mg/kg for compound (A) and from 0.5 to 15 mg/kg for the preferred compounds (B), or 10 to 20 mg/kg for the other compounds (B).

In another embodiment of the process according to the invention, compounds (A) and (B) may be applied in a distinct and separate manner over time. In this case, it is preferred to alternate the applications with an interval, for example of one month between two applications, the first application preferably being made with compound (A).

It is understood that the dosage values which are thus indicated are average values which may vary within a wide range, since, in practice, a formulation having defined doses of compound (A) of 1-N-phenylpyrazole-type derivative and of compound (B) will be administered to animals having relatively different weights. Consequently, the doses actually applied are often smaller or larger by a factor which may be up to 2, 3 or 4 relative to the preferred dose, without entailing any toxic risk for the animal in the case of an overdose, and while at the same time retaining real efficacy, possibly of shorter duration, in the case of an underdose.

The object of this process is non-therapeutic and relates in particular to the cleaning of animal hairs and skin by elimination of the parasites which are present, as well as their residues and dejections. The treated animals thus have hair which is more pleasant to look at and to feel. This also allows one to avoid the development of fleas in the house.

The invention also relates to such a process for therapeutic purposes, which is intended to treat and prevent parasitoses having pathogenic consequences.

In accordance with the present invention, the process described above may also be used to control ectoparasites, in particular ticks.

The subject of the invention is also a composition, in particular one for controlling fleas on small mammals, characterized in that it includes, on the one hand, at least one compound (A) of formula (I) as defined above, and, on the other hand, at least one compound (B) defined above, in doses and proportions which have parasiticidal efficacy on fleas, in a fluid vehicle which is acceptable for the animal and convenient for local application to the skin, preferably localized over a small surface area.

Preferably, in formula (I);

$R_1$ is CN or methyl $R_2$ is $S(O)_n R_3$ $R_3$ is alkyl or haloalkyl $R_4$ represents a hydrogen or halogen atom; or a radical $NR_5 R_6$, $S(O)_m R_7$, $C(O)R_7$, alkyl, haloalkyl or $OR_8$ or a radical —N=C($R_9$) ($R_{10}$)

$R_5$ and $R_6$ independently represent a hydrogen atom or an alkyl, haloalkyl, C(O)alkyl or $S(O)_r$—$CF_3$ radical; or $R_5$ and $R_6$ may together form a divalent alkylene radical which may be interrupted by one or two divalent hetero atoms such as oxygen or sulphur $R_7$ represents an alkyl or haloalkyl radical $R_8$ represents an alkyl or haloalkyl radical or a hydrogen atom $R_9$ represents an alkyl radical or a hydrogen atom $R_{10}$ represents a phenyl or heteroaryl group optionally substituted with one or more halogen atoms or groups such as OH, —O-alkyl, S-alkyl, cyano or alkyl $R_{11}$ and $R_{12}$ represent, independently of each other, a hydrogen or halogen atom $R_{13}$ represents a halogen atom or a haloalkyl, haloalkoxy, $S(O)_q CF_3$ or $SF_5$ group m, n, q and r represent, independently of each other, an integer equal to 0, 1 or 2

X represents a trivalent nitrogen atom or a radical C—$R_{12}$, the other three valency positions of the carbon atom forming part of the aromatic ring with the proviso that when $R_1$ is methyl, then $R_3$ is haloalkyl, $R_4$ is $NH_2$, $R_{11}$ is Cl, $R_{13}$ is $CF_3$ and X is N.

Compounds of formula (I) in which $R_1$ is CN will be selected most particularly. Compounds in which $R_2$ is $S(O)_n R_3$, preferably with n=1, $R_3$ preferably being $CF_3$ or alkyl, for example methyl or ethyl, or alternatively n=0, $R_3$ preferably being $CF_3$, as well as those in which X=C—$R_{12}$, $R_{12}$ being a halogen atom, will also be selected. Compounds in which $R_{11}$ is a halogen atom and those in which $R_{13}$ is haloalkyl, preferably $CF_3$, are also preferred. Within the context of the present invention, compounds which combine two or more of these characteristics will advantageously be selected.

A preferred class of compounds of formula (I) consists of compounds such that $R_1$ is CN, $R_3$ is haloalkyl, $R_4$ is $NH_2$, $R_{11}$ and $R_{12}$ are, independently of each other, a halogen atom, and/or $R_{13}$ is haloalkyl.

In these compounds, $R_3$ preferably represents $CF_3$ or ethyl.

A compound of formula (I) which is most particularly preferred in the invention is 1-[2,6-$Cl_2$ 4-$CF_3$phenyl]3-CN 4-[SO—$CF_3$] 5-$NH_2$ pyrazole.

The two compounds which differ from the above by the following characteristics:

1- n=0, $R_3$=$CF_3$ 2- n=1, $R_3$=ethyl may also be mentioned.

The compounds of formula (I) may be prepared according to one or other of the processes described in patent applications WO-A-87/3781, 93/6089, 94/21606 or European patent application EP-A-0,295,117, or any other process which falls within the competence of a specialist skilled in the art of chemical synthesis. For the chemical preparation of the products of the invention, a person skilled in the art is considered as having at his disposal, inter alia, all of the contents of "Chemical Abstracts" and the documents cited therein.

Among the compounds of IGR type listed above, methoprenes, pyriproxyfens, hydroprene, cyromazine, lufenuron and 1-(2,6-difluorobenzoyl)-3-(2-fluoro-4-(trifluoromethyl)phenylurea are preferred.

Novaluron is also preferred.

The proportions, by weight, of compounds of formula (I) and of compound (B) are preferably between 80/20 and 20/80.

The fluid vehicle may be simple or complex and it is adapted to the route and mode of administration selected.

The compositions for spot-on application can advantageously comprise:

b) a crystallization inhibitor, in particular one which is present in a proportion of from 1 to 20% (W/V), preferably from 5 to 15%, this inhibitor satisfying the test according to which: 0.3 ml of a solution A comprising 10% (W/V) of the compound of formula (I) in the solvent defined in c) below, along with 10% of this inhibitor, are deposited on a glass slide at 20° C. for 24 hours, after which it is observed with the naked eye that there are few or no crystals, in particular fewer than 10 crystals, preferably 0 crystals on the glass slide, c) an organic solvent having a dielectric constant of between 10 and 35, preferably of between 20 and 30, the content of this solvent c) in the overall composition preferably representing the difference to make the composition up to 100%, d) an organic cosolvent having a boiling point of below 100° C., preferably of below 80° C., and having a dielectric constant of between 10 and 40, preferably of between 20 and 30; this cosolvent may advantageously be present in the composition in a d)/c) weight/weight (W/W) ratio of between 1/15 and 1/2. The solvent is volatile, so as to serve in particular as a drying promoter, and is miscible with water and/or with the solvent c).

Although this is not preferred, the composition for spot-on application may optionally comprise water, in particular in a proportion of from 0 to 30% (volume per unit volume, V/V), in particular from 0 to 5%.

The composition for spot-on application may also comprise an antioxidant intended to inhibit air-oxidation, this agent being present in particular in a proportion of from 0.005 to 1% (W/V), preferably from 0.01 to 0.05%.

The compositions according to the invention intended for pets, in particular cats and dogs, are generally applied by being deposited onto the skin ("spot-on" or "pour-on" application); this is generally a localized application over a surface area of less than 10 cm$^2$, especially of between 5 and 10 cm$^2$, in particular at two points and preferably localized between the animal's shoulders. Once deposited, the composition diffuses, in particular over the animal's entire body, and then dries without crystallizing or modifying the appearance (in particular absence of any whitish deposit or dusty appearance) or the feel of the fur.

The compositions for spot-on application according to the invention are particularly advantageous owing to their efficacy, their speed of action and the pleasant appearance of the animal's fur after application and drying.

As organic solvent c) which can be used in the invention, mention may be made in particular of: acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol and diethyl phthalate, or a mixture of at least two of these solvents.

As crystallization inhibitor b) which can be used in the invention, mention may be made in particular of:

polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, acrylic derivatives such as methacrylates and the like, anionic surfactants such as alkaline stearates, in particular sodium, potassium or ammonium stearate; calcium stearate; triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil, cationic surfactants such as water-soluble quaternary ammonium salts of formula $N^+R'R''R'''R'''',Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, amine salts of formula $N^+R'R''R'''$ in which the radicals R are optionally hydroxylated hydrocarbon radicals; octadecylamine hydrochloride is among the cationic surfactants which can be used, nonionic surfactants such as optionally polyoxyethylenated sorbitan esters, in particular polysorbate 80, polyoxyethylenated alkyl ethers; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, amphoteric surfactants such as substituted lauryl compounds of betaine, or preferably a mixture of at least two of these crystallization inhibitors.

In a particularly preferred manner, a crystallization inhibitor couple, namely the combination of a film-forming agent of polymeric type and a surfactant, will be used. These agents will be chosen in particular from the compounds mentioned as crystallization inhibitor b).

Among the film-forming agents of polymeric type which are particularly advantageous, mention may be made of:

the various grades of polyvinylpyrrolidone, polyvinyl alcohols, and copolymers of vinyl acetate and vinylpyrrolidone.

As regards the surfactants, mention will be made most particularly of nonionic surfactants, preferably polyoxyethylenated sorbitan esters and in particular the various grades of polysorbate, for example polysorbate 80.

The film-forming agent and the surfactant may be incorporated, in particular, in similar or identical amounts within the limit of the total amounts of crystallization inhibitor mentioned elsewhere.

The couple thus produced ensures the objectives of absence of crystallization on the hairs and maintenance of the cosmetic appearance of the coat in a note-worthy manner, that is to say without any tendency towards stickiness or to a sticky appearance, despite the high concentration of active material.

As cosolvent d), mention may be made in particular of: absolute ethanol, isopropanol, methanol.

As antioxidant, standard agents are used in particular, such as: butylhydroxyanisole, butylhydroxytoluene, ascorbic acid, sodium metabisulphite, propyl gallate and sodium thiosulphate, or a mixture of not more than two of these agents.

The compositions for spot-on application according to the invention are usually prepared by simple mixing of the constituents as defined earlier; advantageously, to begin with, the active material is mixed in the main solvent and the other ingredients or adjuvants are then added.

The volume applied may be from about 0.3 to 1 ml, preferably about 0.5 ml for cats, and from about 0.3 to 3 ml for dogs, according to the weight of the animal.

In a particularly preferred manner, the composition according to the invention may be in the form of a concentrated emulsion, suspension or solution for spot-on application to a small area of the animal's skin, generally between the two shoulders (spot-on type solution). In a clearly less preferred manner, forms of solution or suspension to be sprayed, forms of solution, suspension or emulsion to be poured or spread onto the animal (pour-on type solution) an oil, a cream, an ointment or any other fluid formulation for topical administration may be provided.

Advantageously, the ready-to-use composition contains a dose of from 0.1 to 40 mg/kg of compound (A) of formula (I) and 0.1 to 40 mg/kg of compound (B).

Preferably, a ready-to-use dosed formulation, in particular one for spot-on application, contains 1 to 20 mg/kg, preferably 2 to 10 mg/kg of compound (A), in particular fipronil, and from 1 to 30 mg/kg, preferably 2 to 10 mg/kg, of preferred compound (B) or 10 to 20 mg/kg of other compound (B).

Advantageously, ready-to-use compositions dosed for 1–10, 10–20 and 20–40 kg animals respectively may be provided.

In another embodiment, provided for separate application over time, a composition may be made in the form of a kit separately combining, in the same packaging, a composition containing a compound of formula (I), in particular fipronil, and a composition containing compound (B), preferably pyriproxyfen, each of the compositions including a vehicle which allows it to be applied onto the skin.

Preferably, each of the two compositions is provided for local spot-on application and, preferably, a container containing just the dose required is provided for each application.

Thus, for example, a kit may contain, in a package, three containers each containing a single dose of composition of compound (A) and three containers each containing a single dose of composition of compound (B), the containers (A) being distinguished from the containers (B) by markings, shapes or colours, as well as a notice specifying that the containers (A) and (B) must be used alternately with an interval, for example, of one month, and starting, for example, with a container (A).

The compositions according to the invention, in particular those for spot-on application, have proven to be extremely effective for the very long-lasting treatment of fleas on mammals, and in particular small mammals such as cats and dogs.

The discovery that the compound (A), such as fipronil, dissolves in the sebum so as to cover the entire animal and becomes concentrated in the sebaceous glands, from which it is gradually released over a very long period, is a plausible explanation of this long-lasting efficacy for these compositions, and could perhaps also explain the long-lasting action of the associated compound (B).

They also have a certain efficacy against other parasitic insects and, in particular, ticks, and it is understood that the application of the composition according to the invention may be extended to the treatment of ectoparasites, or even endoparasites for which the composition proves to have real utility capable of being obtained practically, according to the criteria of the veterinary art.

Thus, for example, a composition based on fipronil and fluazuron may also be used in particular against ticks.

Where appropriate, the composition according to the invention may also comprise another insecticide, and in particular imidaclopride.

The subject of the invention is also the use of at least one compound (A) of formula (I) and of at least one compound (B) of IGR type, as defined above, for the preparation of a composition as defined above.

Other advantages and characteristics of the invention will become apparent on reading the description which follows, which is given by way of non-limiting example.

The composition preparation example which follows includes, as compound (A) of formula (I), the compound known as fipronil.

By way of example to prepare a composition for local application to the skin according to the invention, the following components may advantageously be mixed together:

a1—compound (B) in a proportion of from 1 to 20% (percentage as a weight per unit volume W/V)

a2—compound (A) of formula (I), in a proportion of from 1 to 20%, preferably 5 to 15% (percentage as a weight per unit volume W/V).

By way of example, the compositions according to the invention comprise the following concentrations (W/V) of compounds (A) and (B) in a liquid medium comprising a representative of each of the components b, c and d. The total volume is 1 ml.

EXAMPLE 1 fipronil 10%
pyriproxyfen 5%

EXAMPLE 2 fipronil 5%
pyriproxyfen 5%

EXAMPLE 3 fipronil 5%
pyriproxyfen 20%

EXAMPLE 4 fipronil 10%
methoprene 30%

EXAMPLE 5 fipronil 10%
1-(2,6-difluorobenzoyl)-3-(2-fluoro-4-trifluoromethyl) phenylurea 5%.

Cats are infested with 100 fleas each, and are then reinfested every 10 days. Concomitant with the first manifestation, they receive a local skin application of 0.1 ml/kg of the composition according to Example 1. Two months after the treatment and ten days after the last infestation, no fleas are detected and the eggs collected are found to be non-viable.

Dogs treated according to the same procedure with compositions according to Examples 1 and 2 show the same efficacy of treatment two months after application of the composition.

What is claimed is:

1. A synergistic spot-on composition for the long lasting protection against fleas and ticks on mammals which comprises synergistic effective amounts of Fipronil synergistic amount of a compound which mimics juvenile hormones and at least one customary spot-on formulation adjuvant.

2. The synergistic composition according to claim 1 wherein the compound which mimics juvenile hormones is selected from the group consisting of azadirachtin, diofenolan, fenoxycarb, hydroprene, kinoprene, methoprene, pyriproxyfen, tetrahydroazadirachtin and 4-chloro-2-(2-chloro-2-methyl-propyl)-5-(6-iodo-3-pyridylmethoxy) pyridizine-3(2II)-one.

3. The synergistic composition according to claim 1, wherein the compound which mimics juvenile hormones is methopren or pyriproxyfen.

4. The synergistic composition according to claim 1, wherein the compound which mimics juvenile hormones is methopren.

5. A synergistic spot-on composition for long-lasting protection against fleas on mammals comprising synergistic amounts of at least one compound (A) of the formula

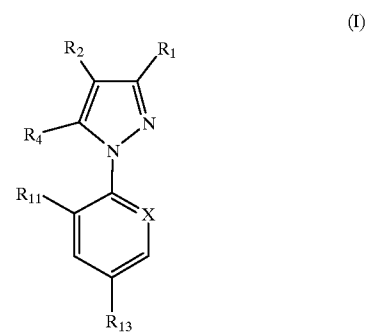

(I)

in which:

$R_1$ is CN or methyl or a halogen atom;

$R_2$ is $S(O)_n R_3$ or 4,5-dicyanoimidazol-2-yl or haloalkyl;

$R_3$ is alkyl or haloalkyl;

$R_4$ represents a hydrogen or halogen atom; or a radical $NR_5R_6$, $S(O)_m R_7$, $C(O)R_7$, $C(O)O—R_7$, alkyl, haloalkyl or $OR_8$ or a radical $—N=C(R_9)(R_{10})$;

$R_5$ and $R_6$ independently represent a hydrogen atom or an alkyl, haloalkyl, C(O)alkyl, alkoxycarbonyl or $S(O)_r—CF_3$ radical; $R_6$ and $R_6$ may together form a divalent alkylene radical which may be interrupted by one or two divalent hetero atoms;

$R_7$ represents an alkyl or haloalkyl radical;

$R_8$ represents an alkyl or haloalkyl radical or a hydrogen atom;

$R_{10}$ represents a phenyl or heteroaryl group optionally substituted with one or more halogen atoms or groups such as OII, —O-alkyl, S-alkyl, cyano or alkyl;

$R_{11}$ and $R_{12}$ represent, independently of each other, a hydrogen or halogen atom, or optionally CN or $NO_2$;

$R_{13}$ represents a halogen atom or a haloalkyl, haloalkoxy, $S(O)_q CF_3$ or $SF_5$ group;

m, n, q and r represent, independently of each other, an integer equal to 0, 1 or 2;

X represents a trivalent nitrogen atom or a radical C—$R_{12}$, the other three valency positions of the carbon atom forming part of the aromatic ring;

with the proviso that when $R_1$ is methyl, then $R_3$ is haloalkyl, $R_4$ is $NH_2$, $R_{11}$ is Cl, $R_{13}$ is $CF_3$ and X is N; or $R_2$ is 4,5-dicyanoimidazol-2-yl, $R_4$ is Cl, $R_{11}$ is Cl, $R_{13}$ is $CF_3$ and X is =C—Cl;

a synergistic amount of at least one ovicidal compound (B), of insect growth regulator (IGR) type, in a fluid vehicle which is acceptable to the animal and suitable for local application to the skin; and at least one customary spot-on formulation adjuvant.

6. Composition according to claim 5, characterized in that the compound of formula (I) is such that:

$R_1$ is CN or methyl $R_2$ is $S(O)_n R_3$ $R_3$ is alkyl or haloalkyl $R_4$ represents a hydrogen or halogen atom; or a radical $NR_5 R_6$, $S(O)_m R_7$, $C(O)R_7$, alkyl, haloalkyl or $OR_8$ or a radical —N=C($R_9$) ($R_{10}$)

$R_5$ and $R_6$ independently represent a hydrogen atom or an alkyl, haloalkyl, C(O)alkyl or $S(O)_r$—$CF_3$ radical; or $R_5$ and $R_6$ may together form a divalent alkylene radical which may be interrupted by one or two divalent hetero atoms such as oxygen or sulphur $R_7$ represents an alkyl or haloalkyl radical $R_8$ represents an alkyl or haloalkyl radical or a hydrogen atom $R_9$ represents an alkyl radical or a hydrogen atom $R_{10}$ represents a phenyl or heteroaryl group optionally substituted with one or more halogen atoms or groups such as OH, —O-alkyl, S-alkyl, cyano or alkyl $R_{11}$ and $R_{12}$ represent, independently of each other, a hydrogen or halogen atom $R_{13}$ represents a halogen atom or a haloalkyl, haloalkoxy, $S(O)_q CF_3$ or $SF_5$ group m, n, q and r represent, independently of each other, an integer equal to 0, 1 or 2

X represents a trivalent nitrogen atom or a radical C—$R_{12}$, the other three valency positions of the carbon atom forming part of the aromatic ring with the proviso that when $R_1$ is methyl, then $R_3$ is haloalkyl, $R_4$ is $NH_2$, $R_{11}$ is Cl, $R_{13}$ is $CF_3$ and X is N.

7. Composition according to claim 6, in which the compound of formula (I) is such that $R_1$ is CN, $R_3$ is haloalkyl, $R_4$ is $NH_2$, $R_{11}$ and $R_{12}$ are, independently of each other, a halogen atom, and/or $R_{13}$ is haloalkyl.

8. Composition according to claim 7, wherein X is C—$R_{12}$.

9. Composition according to claim 6, in which the compound of formula (I) is: 1-[2,6-$Cl_2$ 4-$CF_3$ phenyl] 3-CN 4-[SO-$CF_3$]5-$NH_2$ pyrazole, commonly known as Fipronil.

10. Composition according to claim 6, characterized in that the compound (B) is a compound which mimics juvenile hormones or a chitin-synthesis inhibitor.

11. Composition according to claim 10, characterized in that the compound of IGR type is chosen from methoprenes, pyriproxyfens, lufenuron, hydroprene, cryomazine and 1-(2,6-difluorobenzoyl)-3-(2-fluoro-4-(trifluoromethyl) phenylurea.

12. Composition according to claim 10 wherein the compound which mimics juvenile hormones is selected from the group consisting of azadirachtin, diofenolan, fenoxycarb, hydroprene, kinoprene, methoprene, pyriproxyfen, tetrahydroazadirachtin, and 4-chloro-2-(2-chloro-2-methyl-propyl)-5-(6-iodo-3-pyridylmethoxy)-pyridizine-3(2H)-one.

13. Composition according to claim 10 wherein the chitin-synthesis inhibitor is selected from the group consisting of chlorfluazuron, cyromazine, diflubenzuron, fluazuron, flucycloxuron, flufenoxuron, hexaflumuron, lufenuron, tebufenozide, teflubenzuron, triflumuron, 1-(2,6-difluorobenzoyl)-3-(2-fluoro-4-(trifluoromethyl) phenylurea,1-(2,6-difluoro-benzoyl)-3-(2-fluoro-4-(1,1,2,2-tetrafluoroethoxy)-phenylurea and 1-(2,6-difluoro-benzoyl)-3-(2-fluoro-4-trifluoro-methyl)phenylurea.

14. Composition according to claim 6, characterized in that the proportions, by weight, of compounds (A) of formula (I) and of compounds of type (B) are between 80/20 and 20/80.

15. Composition according to claim 6, characterized in that it contains a dose of from 0.1 to 40 mg/kg of compound (A) and from 0.1 to 40 mg/kg of compound (B).

16. Composition according to claim 15, characterized in that it contains a dose of from 1 to 20 mg/kg, in particular from 2 to 10 mg/kg, of compound (A) and from 1 to 30 mg/kg, in particular 2 to 20 mg/kg, of compound (B).

17. Composition according to claim 5, characterized in that the compound of formula (I) is such that $R_1$ is CN.

18. Composition according to claim 5, characterized in that the compound of formula (I) is such that $R_{13}$ is haloalkyl.

19. Composition according to claim 5, characterized in that the compound of formula (I) is such that $R_2$ is $S(O)_n R_3$, and $R_3$ is $CF_3$ or alkyl.

20. Composition according to claim 5, characterized in that the compound of formula (I) is such that X is C—$R_{12}$ with $R_{12}$ being a halogen atom.

21. Composition according to claim 5, in which the compound of formula (I) is such that $R_1$ is CN, $R_3$ is haloalkyl, $R_4$ is $NH_2$, $R_{11}$ and $R_{12}$ are, independently of each other, a halogen atom, and/or $R_{13}$ is haloalkyl.

22. Composition according to claim 5, in which the compound of formula (I) is: 1-[2,6-$Cl_2$ 4-$CF_3$ phenyl] 3-CN 4-[SO—$CF_3$]5-$NH_2$ pyrazole, commonly known as Fipronil.

23. Composition according to claim 5, in which the compound of formula (I) is one of the following compounds:
1: 1-[2,6-$Cl_2$ 4-$CF_3$ phenyl] 3-CN 4-[S—$CF_3$]5-$NH_2$ pyrazole, commonly known as Fipronil
2: 1-[2,6-$Cl_2$ 4-$CF_3$ phenyl] 3-CN 4-[SO—$C_2H_5$]5-$NH_2$ pyrazole.

24. Composition according to claim 5, characterized in that the compound (B) is a compound which mimics juvenile hormones or a chitin-synthesis inhibitor.

25. Composition according to claim 24, characterized in that the compound of IGR type is chosen from methoprenes, pyriproxyfens, lufenuron, hydroprene, cryomazine and 1-(2,6-difluorobenzoyl)-3-(2-fluoro-4-(trifluoromethyl) phenylurea.

26. Composition according to claim 24 wherein the compound which mimics juvenile hormones is selected from the group consisting of azadirachtin, diofenolan, fenoxycarb, hydroprene, kinoprene, methoprene, pyriproxyfen, tetrahydroazadirachtin, and 4-chloro-2-(2-chloro-2-methyl-propyl)-5-(6-iodo-3-pyridylmethoxy)-pyridizine-3(2H)-one.

27. Composition according to claim 24 wherein the chitin-synthesis inhibitor is selected from the group consisting of chlorfluazuron, cyromazine, diflubenzuron, fluazuron, flucycloxuron, flufenoxuron, hexaflumuron, lufenuron, tebufenozide, teflubenzuron, triflumuron, 1-(2,6-difluorobenzoyl)-3-(2-fluoro-4-(trifluoromethyl) phenylurea,1-(2,6-difluoro-benzoyl)-3-(2-fluoro-4-(1,1,2,2-tetrafluoroethoxy)-phenylurea and 1-(2,6-difluoro-benzoyl)-3-(2-fluoro-4-trifluoro-methyl)phenylurea.

28. Composition according to claim 5, characterized in that compound (B) is novaluron.

29. Composition according to claim 5, characterized in that the proportions, by weight, of compounds (A) of formula (I) and of compounds of type (B) are between 80/20 and 20/80.

30. Composition according to claim 5, characterized in that it also comprises a crystallization inhibitor (b), which is present in a proportion of from 1 to 20% (W/V).

31. Composition according to claim 30, characterized in that the crystallization inhibitor (b) is selected from the group consisting of:
polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, methacrylates and other acrylic derivatives,
anionic surfactants,
cationic surfactants,
amine salts of formula $N^+R'R''R'''$ in which the radicals R are optionally hydroxylated hydrocarbon radicals;
nonionic surfactants;
amphoteric surfactants; and
a mixture of at least two of these crystallization inhibitors.

32. Composition according to claim 31 wherein the anionic surfactant is selected from the group consisting of sodium, potassium or ammonium stearate or other alkaline stearates; calcium stearate; triethanolamine stearate; sodium abietate; sodium lauryl sulphate, sodium cetyl sulphate or other alkyl sulphates; sodium dodecylbenzenesulphonate, sodium dioctylsulphosuccinate; and fatty acids derived from coconut oil or other fatty acids.

33. Composition according to claim 31 wherein the cationic surfactant is selected from the group consisting of water-soluble quaternary ammonium salts of formula $N^+R'R''R'''R'''',Y^-$ in which the radicals R are optionally hydroxylated hydrocarbon radicals and $Y^-$ is an anion of a strong acid; cetyltrimethyl-ammonium bromide; amine salts of formula $N^+R'R''R'''$ in which the radicals R are optionally hydroxylated hydrocarbon radicals; and octadecylamine hydrochloride.

34. Composition according to claim 31 wherein the nonionic surfactant is selected from the group consisting of polysorbate 80, polyoxyethylenated alkyl ethers and other optionally polyoxyethylenated sorbitan esters; polyethylene glycol stearate, polyoxyethylenated derivatives of castor oil, polyglycerol esters, polyoxyethylenated fatty alcohols, polyoxyethylenated fatty acids, and copolymers of ethylene oxide and propylene oxide.

35. Composition according to claim 31 wherein the amphoteric surfactant comprises substituted lauryl compounds of betaine.

36. Composition according to claim 30, characterized in that it comprises a crystallization inhibitor couple formed by the combination of a film-forming agent of polymeric type and a surfactant.

37. Composition according to claim 36, characterized in that the film-forming agent is selected from the group consisting of:
the various grades of polyvinylpyrrolidone,
polyvinyl alcohols, and
copolymers of vinyl acetate and vinyl pyrrolidone,
and in that the surfactant is selected from the group consisting of polyoxyethylenated sorbitan esters, various grades of polysorbate, and other non-ionic surfactants.

38. Composition according to claim 5, characterized in that it comprises an organic solvent (c) having a dielectric constant of between 10 and 35.

39. Composition according to claim 38, characterized in that the organic solvent (c) is selected from the group consisting of acetone, acetonitrile, benzyl alcohol, butyldiglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, diethylene glycol monoethyl ether, ethylene glycol, diethyl phthalate, and a mixture of at least two of these solvents.

40. Composition according to claim 38, characterized in that it also comprises an organic co-solvent (d) having a boiling point below 100° C., and having a dielectric constant of between 10 and 40, which is miscible with water and/or with the solvent (c), this co-solvent being present in a co-solvent (d)/solvent (c) weight/weight (W/W) ratio of between 1/15 and 1/2.

41. Composition according to claim 40, characterized in that the co-solvent (d) is chosen from absolute ethanol, isopropanol and methanol.

42. Composition according to claim 1, wherein the composition is applied to a zone with a surface area of less than 10 cm$^2$.

43. Composition according to claim 40 wherein the composition is applied at two points between the animal's shoulders.

44. Composition according to claim 5, characterized in that it contains a dose of from 0.1 to 40 mg/kg of compound (A) and from 0.1 to 40 mg/kg of compound (B).

45. Composition according to claim 44, characterized in that it contains a dose of from 1 to 20 mg/kg of compound (A) and from 1 to 30 mg/kg of compound (B).

46. Composition according to claim 5, characterized in that it affords protection for 2 to 3 months.

47. Composition according to claim 5 wherein the mammals protected by the composition comprise cats and dogs.

48. The composition according to claim 5, wherein the composition is a spot-on type.

49. A method for controlling fleas and ticks on mammals over a long duration of time which comprises locally applying to the skin of said mammal a synergistically effective amount of a synergistic composition according to claim 5.

50. The method according to claim 49, wherein the mammals are cats and dogs.

51. The method according to claim 49 wherein, the dose of the composition is from 1 to 20 mg/kg of compound (A) and 1 to 30 mg/kg of compound (B).

52. The method according to claim 49, wherein it contains a dose of from 0.1 to 40 mg/kg of compound (A) and from 0.1 to 40 mg/kg of compound (B).

53. The method according to claim 49, wherein it contains a dose of from 1 to 20 mg/kg.

54. The method of claim 49 wherein in the compound $R_1$ is CN.

55. The method of claim 49 wherein in the compound $R_{13}$ is haloalkyl.

56. The method of claim 49 wherein in the compound $R_{13}$ is $CF_3$.

57. The method of claim 49 wherein in the compound $R_2$ is $S(O)_n R_3$.

58. The method of claim 49 wherein in the compound n=1 and $R_3$ is methyl, ethyl or $CF_3$.

59. The method of claim 49 wherein in the compound n=0 and $R_3$ is $CF_3$.

60. The method of claim 49 wherein in the compound X is C—$R_{12}$ and is a halogen atom.

61. The method of claim 49 wherein in the compound $R_1$ is CN, and/or $R_3$ is haloalkyl, and/or $R_1$ is $NH_2$, and/or $R_{11}$ and $R_{12}$ are, independently of each other, a halogen atom, and/or $R_{13}$ is haloalkyl.

62. The method according to claim 49, wherein the synergistic composition comprises synergistic effective amounts of Fipronil and a compound which mimics juvenile hormones.

63. The method according to claim 62, wherein the compound which mimics juvenile hormones is selected from the group consisting of azadirachtin, diofenolan, fenoxycarb, hydroprene, kinoprene, methoprene, pyriproxyfen, tetrahydroazadirachtin and 4-chloro-2-2-chloro-2-methyl-propyl)-5-(6-iodo-3-pyridylmethoxy) pyridizine-3(2H)-one.

64. The method according to claim 62, wherein the compound which mimics juvenile hormones is methopren or pyriproxyfen.

65. The method according to claim 62, wherein the compound which mimics juvenile hormones is methopren.

66. The method according to claim 49, wherein the duration is two months.

67. The method according to claim 49, wherein the duration is three months.

68. The method according to claim 67, wherein the synergistic combination comprises synergistic effective amounts of Fipronil and methoprene.

69. A method for distributing an active agent over a mammal's body and/or in the sebaceous glands of said mammal and thereby control fleas and ticks for a long period of time which comprises applying to the skin of said mammal a synergistic composition according to claim 5.

70. A kit comprising, separately, in the same packaging, at least one container containing a synergist amount of a compound (A) according to claim 1 and at least one customary spot-on formulation adjuvant and at least one container containing a synergistic amount of a compound (B) according to claim 1 and at least one customary spot-on formulation adjuvant, and a notice specifying that the containers are to be used alternately with an interval.

* * * * *

UNITED STATES PATENT AND TRADEMARK OFFICE
CERTIFICATE OF CORRECTION

PATENT NO.    : 6,096,329
DATED         : August 1, 2000
INVENTOR(S)   : Philippe Jeannin It is certified that error appears in the above-identified patent and that said Letters Patent is hereby corrected as shown below:

<u>Column 12,</u>
Lines 49-50, "1: 1-[2,6-$Cl_2$ 4-$CF_3$ phenyl] 3-CN 4-[S-$CF_3$]5-$NH_2$ pyrazole, commonly known as Fipronil" should read -- 1: 1-[2,6-$Cl_2$ 4-$CF_3$ phenyl] 3-CN 4-[SO-$CF_3$]5-$NH_2$ pyrazole, commonly known as Fipronil --.

Signed and Sealed this

Ninth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,096,329
DATED         : August 1, 2000
INVENTOR(S)   : Philippe Jeannin It is certified that error appears in the above-identified patent and that said Letters Patent is hereby corrected as shown below:

Column 10,
Line 63, insert -- $R_9$ represents an alkyl radical or a hydrogen atom; --.

Signed and Sealed this

Seventeenth Day of May, 2005

JON W. DUDAS
*Director of the United States Patent and Trademark Office*

US006096329C1

(12) EX PARTE REEXAMINATION CERTIFICATE (8587th)

United States Patent
Jeannin

(10) Number: US 6,096,329 C1
(45) Certificate Issued: Oct. 4, 2011

(54) INSECTICIDAL COMBINATION TO CONTROL MAMMAL FLEAS, IN PARTICULAR FLEAS ON CATS AND DOGS

(75) Inventor: Philippe Jeannin, Tournefeuille (FR)

(73) Assignee: Merial, Lyons (FR)

Reexamination Request:
No. 90/011,152, Aug. 10, 2010

Reexamination Certificate for:
Patent No.: 6,096,329
Issued: Aug. 1, 2000
Appl. No.: 08/863,692
Filed: May 27, 1997

Certificate of Correction issued Dec. 9, 2003.

Certificate of Correction issued May 17, 2005.

Related U.S. Application Data

(63) Continuation-in-part of application No. 08/692,113, filed on Aug. 5, 1996, now abandoned.

(51) Int. Cl.
*A01N 43/56* (2006.01)

(52) U.S. Cl. .................. 424/405; 514/407; 514/875
(58) Field of Classification Search .................. None
See application file for complete search history.

(56) References Cited

U.S. PATENT DOCUMENTS

| | | | |
|---|---|---|---|
| 4,166,107 A | 8/1979 | Miller et al. .............. 424/405 |
| 4,395,407 A | 7/1983 | Ballany et al. ............. 514/80 |
| 4,607,050 A * | 8/1986 | Kieran et al. .............. 514/520 |
| 4,764,529 A | 8/1988 | Naik et al. ................ 514/531 |
| 4,804,675 A | 2/1989 | Jensen-Korte et al. ....... 514/407 |
| 5,045,536 A | 9/1991 | Baker ...................... 514/63 |
| 5,053,227 A | 10/1991 | Chiang et al. ............. 424/448 |
| 5,059,593 A | 10/1991 | Stendel et al. ............ 514/65 |
| 5,120,716 A * | 6/1992 | Miyazawa et al. .......... 514/23 |
| 5,141,938 A | 8/1992 | Lindner et al. ............ 514/242 |
| 5,192,787 A * | 3/1993 | Bowers et al. ............. 514/404 |
| 5,194,264 A | 3/1993 | Van Tonder ............... 424/405 |
| 5,232,940 A * | 8/1993 | Hatton et al. ............. 514/407 |
| 5,256,679 A * | 10/1993 | Minamida et al. .......... 514/357 |
| 5,266,234 A | 11/1993 | Ho et al. ................. 424/411 |
| 5,439,924 A | 8/1995 | Miller .................... 514/345 |
| 5,468,765 A * | 11/1995 | Banks et al. .............. 514/395 |
| 5,482,956 A | 1/1996 | Lunkenheimer et al. .... 514/394 |
| 5,567,429 A * | 10/1996 | Senbo .................... 424/405 |
| 5,612,047 A | 3/1997 | Duffy et al. .............. 424/405 |
| 5,777,075 A | 7/1998 | Scherkenbeck et al. ..... 530/330 |
| 5,939,441 A | 8/1999 | Stetter et al. ............. 514/341 |
| 6,395,765 B1 | 5/2002 | Etchegaray ............... 514/407 |
| 6,565,450 B1 | 5/2003 | Nakahara ................. 514/227.2 |

FOREIGN PATENT DOCUMENTS

| | | |
|---|---|---|
| CA | 1069823 A1 | 1/1980 |
| EP | 0 271 923 A1 | 6/1988 |
| EP | 0 295 117 A1 | 12/1988 |
| EP | 0 051 786 A | 5/1992 |
| EP | 0 500 209 | 8/1992 |
| EP | 516 590 | 12/1992 |
| EP | 0 234 119 B1 | 8/1994 |
| EP | 0 682 869 A1 | 11/1995 |
| FR | 2 713 889 A1 | 6/1995 |
| JP | 06-065219 | 3/1994 |
| WO | WO 87/03781 | 7/1987 |
| WO | WO 90/09738 | 9/1990 |
| WO | WO 91/13545 | 9/1991 |
| WO | WO 93/02058 | 2/1993 |
| WO | WO 93/06089 | 4/1993 |
| WO | WO 93/20799 | 10/1993 |
| WO | WO 94/21606 | 9/1994 |
| WO | WO 94/26113 | 11/1994 |
| WO | WO 95/04746 | 2/1995 |
| WO | WO 95/33380 | 12/1995 |
| WO | WO 96/16544 | 6/1996 |
| WO | PCT/FR96/01521 | 6/1997 |
| ZA | 884179 | 6/1988 |

OTHER PUBLICATIONS

"Evaluating a Synergized Pyrethrin/(S)–methoprene Spray Against Feline Flea Infestations," Donahue & Young, *Veterinary Medicine* Oct. 1992, pp. 1999–1007.

"Frontline Combo Spot–On Dog M" Summary of Product Characteristics, Jul. 2, 2008, AN2218/2007.

Frontline Spray Brochure "Frontline No Other Flea Treatment Works Like It or Lasts Like It," Mar. 1996.

Dictionaire Medicaments Veterinaires, $14^{th}$ edition, 2007, pp. 1083, Wolters Kluwer, France.

Dictionaire Medicaments Veterinaires, $14^{th}$ edition, 2007, pp. 638–639, Wolters Kluwer, France.

"Field Efficacy of a Mechanical Pump Spray Formulation Containing 0.25% Fipronil in the Treatment and Control of Flea Infestation and Associated Dermatological Sings in Dogs and Cats," Postal et al., *Veterinary Dermatology*, 1995, vol. 6(3), pp. 153–158.

"Ovicidal Effect on Cat Flea, Ctenocephalides felis (Bouche) of Treating Fur of Cats and Dogs with Methoprene,*"* Olsen, Alice, International Pest Control, Jan./Feb. 1995, pp. 10–14.

"Pharmacologic Profile of Methoprene, an Insect Growth Regulator, in Cattle, Dogs and Cats," Garg et al., *Journal of the American Veterinary Medical Association*, 1989, vol. 194(30, pp. 410–412.

(Continued)

*Primary Examiner*—Brenda Brumback

(57) ABSTRACT

Process and composition, in particular for controlling fleas on small mammals, characterized in that the composition includes, on the one hand, at least one insecticide of 1-N-arylpyrazole type, in particular fipronil, and, on the other hand, at least one compound of IGR (insect growth regulator) type, in doses and proportions which are parasiticidally effective on fleas, in a fluid vehicle which is acceptable for the animal and convenient for local application to the skin, preferably localized over a small surface area.

OTHER PUBLICATIONS

"Pharmaceutical Skin Penetration Enhancement" edited by Kenneth A. Walters and Jonathan Hadgraft, 1993 Marcel Dekker, Inc. New York; Chapter 5: pp. 113–116, 129–131, 136–139; Chapter 10: pp. 229–242; Chapter 11: pp. 243–267; and Chapter 16: pp. 345–364.

Summary of Product Characteristics for Vet Kem Dog Spray; date of approval—Apr. 11, 2003.

The Merck Veterinary Manual, 7$^{th}$ Edition 1991, Merck & Co., Inc., Rahway, NJ; pp. 796–797; 1497–1502.

The Pesticide Manual, 10$^{th}$ Edition 1994, The British Crop Protection Council Surrey, The United Kingdom and The Royal Society of Chemistry, Cambridge, The United Kingdom; Foreward and pp. 296, 463, 591–592, 680–681 and 860.

Jeannin et al., Proceedings of the British Small Animal Veterinary Association Congress, Birmingham; B.S.A.V.A.; 1994, p. 174.

"Formulation of Corticosteroids Using Transcutol as a Cosolvent: In–vitro, Ex–vivo and In–vivo rat Studies," Panchagnula and Ritschel, *J. Pharm. Pharmacol.*, 1991, 43, pp. 609–615.

"Developmental Toxicity of Four Glycol Ethers Applied Cutaneously to Rats," Hardin et al., *Environmental Health Perspectives*, 1984, vol. 57, pp. 69–74.

"Bioavailabity Assessment of Topical Delivery Systems: Effect of Vehicle Evaporation Upon In Vitro Delivery of Minoxidil from Solution Formulations," Chiang et al., *International Journal of Pharmaceutics*, 1989, 55, 229–236.

"Skin Penetration Enhancement," Hadgraft & Walters, *Journal of Dermatological Treatment*, 1994, 5, pp. 43–47.

"Effect of Supersaturation on Membrane Transport: 2. Piroxicam," Pellett et al., *International Journal of Pharmaceutics*, 1994, 117, pp. 1–6.

"Methods of Measuring, and Factors Affecting, Percutaneous Adsorption," Grasso & Lansdown, *J. Soc. Cosmet. Chem.*, 1972, 23, pp. 481–521.

"Transfollicular Drug Delivery," Lauer et al., Pharmaceutical Research, 1995, vol. 12(2), 179–186.

"Follicles Play an Important Role in Percutaneous Adsorption," Illel et al., *Journal of Pharmaceutical Sciences*, 1991, 80(5), pp. 424–427.

"Role of Transepidermal and Transfollicular Routes in Percutaneous Adsorption of Steroids; In Vitro Studies on Human Skin," Hueber et al., *Skin Pharmacol.* 1994, 7, pp. 237–244.

"Enhancement of Percutaneous Adsorption by the Use of Volatile:Nonvolatile Systems as Vehicles," *Journal of Pharmaceutical Sciences*, 1969, 58(9), pp. 1098–1102.

"Extended Efficacy Spectrum of Azole Pesticides," *Research Disclosure*, No. 380, Dec. 1, 1995; p. 802.

*Eur. J. Plant Pathol.*, 1995, vol. 101 Suppl. 1, p. 8.

"Efficacia del Fipronil in Formulazione Spray (Frontline RM) Net Trattamento Delle Infestazioni da Pulci e da Zecche nel Cane," Genchi et al., *Professione Veterinaria*, 1995, No. i., Supplement, pp. 19–22.

"Efficacia di Una Formulazione Spray a Base di Fiprinok Allo 0,25% nel Trattamento e Nella Prevenzione Delle Infestazioni da Pulci nel Cane e nel Gatto," Postal et al., *Proffisone Veterinaria*, 1995, No. 1, pp. 17–18.

\* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 1 is confirmed.

Claims 6-11, 13-14, 17-25, 27-28, 42-48, 54-62, and 68 are cancelled.

Claims 2-5, 12, 15, 26, 63-65 and 70 are determined to be patentable as amended.

Claims 16, 29-41, 49-53, 66-67 and 69, dependent on an amended claim, are determined to be patentable.

New claims 71-108 are added and determined to be patentable.

2. The synergistic composition according to claim 1 wherein the compound which mimics juvenile hormones is selected from the group consisting of azadirachtin, diofenolan, fenoxycarb, hydroprene, kinoprene, methoprene, pyriproxyfen, tetrahydroazadirachtin and [4-chloro-2-(2-chloro-2-methyl-propyl)-5-(6-iodo-3-pyridylmethoxy) pyridizine-3(2H)-one] *4-chloro-2-(2-chloro-2-methyl-propyl)-5-(6-iodo-3-pyridylmethoxy) pyridizine-3(2H)-one*.

3. The synergistic composition according to claim 1, wherein the compound which mimics juvenile hormones is [methopren] *methoprene* or pyriproxyfen.

4. The synergistic compositon according to claim 1, wherein the compound which mimics juvenile hormones is [methopren] *methoprene*.

5. A synergistic spot-on composition for long-lasting protection against fleas on mammals comprising synergistic amounts of at least one compound (A) [of the formula

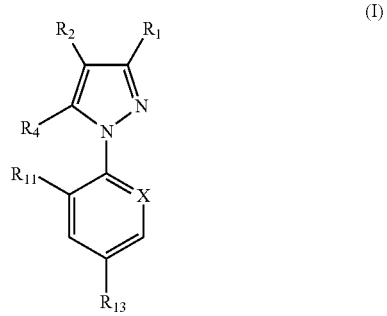

in which:
R$_1$ is CN or methyl or a halogen atom;
R$_2$ is S(O)$_n$R$_3$ or 4,5-dicyanoimidazol-2-yl or haloalkyl;
R$_3$ is alkyl or haloalkyl;
R$_4$ represents a hydrogen or halogen atom; or a radical NR$_5$R$_6$, S(O)$_m$R$_7$, C(O)R$_7$, C(O)O—R$_7$, alkyl, haloalkyl or OR$_8$ or a radical —N═C(R$_9$) (R$_{10}$);

R$_5$ and R$_6$ independently represent a hydrogen atom or an alkyl, haloalkyl, C(O)alkyl, alkoxycarbonyl or S(O)$_r$—CF$_3$ radical; R$_6$ and R$_6$ may together form a divalent alkylene radical which may be interrupted by one or two divalent hetero atoms;

R$_7$ represents an alkyl or haloalkyl radical;

R$_8$ represents an alkyl or haloalkyl radical or a hydrogen atom;

R$_9$ represents an alkyl radical or a hydrogen atom;

R$_{10}$ represents a phenyl or heteroaryl group optionally substituted with one or more halogen atoms or groups such as OH, —O-alkyl, S-alkyl, cyano or alkyl;

R$_{11}$ and R$_{12}$ represent, independently of each other, a hydrogen or halogen atom, or optionally CN or NO$_2$;

R$_{13}$ represents a halogen atom or a haloalkyl, haloalkoxy, s(O)$_q$CF$_3$ or SF$_5$ group;

m, n, q and r represent, independently of each other, an integer equal to 0, 1 or 2;

X represents a trivalent nitrogen atom or a radical C—R$_{12}$, the other three valency positions of the carbon atom forming part of the aromatic ring;

with the proviso that when R$_1$ is methyl, then R$_3$ is haloalkyl, R$_4$ is NH$_2$, R$_{11}$ is Cl, R$_{13}$ is CF$_3$ and X is N; or R$_2$ is 4,5-dicyanomidazol-2-yl, R$_4$ is Cl, R$_{11}$ is Cl, R$_{13}$ is CF$_3$ and X is ═C—Cl;]
*wherein said compound (A) is fipronil, and*
a synergistic amount of at least one ovicidal compound (B), [of insect growth regulator (IGR) type] *wherein said compound (B) is a compound which mimics juvenile hormones*, in a fluid vehicle which is acceptable to the animal and suitable for local application to the skin; and at least one customary spot-on formulation adjuvant.

12. Composition according to claim [10] *5* wherein the compound which mimics juvenile hormones is selected from the group consisting of azadirachtin, diofenolan, fenoxycarb, hydroprene, kinoprene, methoprene, pyriproxyfen, tetrahydroazadirachtin, and 4-chloro-2-(2-chloro-2-methyl-propyl)5-(6-iodo-3-pyridylmethoxy)-pyridizine-3(2H)-one.

15. Composition according to claim [6] *5*, characterized in that it contains a dose of from 0.1 to 40 mg/kg of compound (A) and from 0.1 to 40 mg/kg of compound (B).

26. Composition according to claim [24] *5*,wherein the compound which mimics juvenile hormones is [selected from the group consisting of azadirachtin, diofenolan, fenoxycarb, hydroprene, kinoprene,] methoprene[, pyriproxyfen, tetrahydroazadirachtin, and 4-chloro-2-(2-chloro-2-methyl-propyl)-5-(6-iodo-3-pyridylmethoxy)-pyridizine-3(2H)-one].

63. The method according to claim [62] *49*, wherein the compound which mimics juvenile hormones is selected from the group consisting of azadirachtin, diofenolan, fenoxycarb, hydroprene, kinoprene, methoprene, pyriproxyfen, tetrahydroazadirachtin and 4-2chloro-2--chloro-2methyl-propyl)-5-(6-iodo-3-pyridylmethoxy) pyridizine-3(2H)-one.

64. The method according to claim [62] *49*, wherein the compound which mimics juvenile hormones is [methopren] *methoprene* or pyriproxyfen.

65. The method according to claim [62] *49*, wherein the compound which mimics juvenile hormones is [methopren] *methoprene*.

70. A kit comprising, separately, in the same packaging, at least one container containing a [synergist] *synergistic* amount of a compound (A) according to claim 1 and at least one customary spot-on formulation adjuvant and at least one container containing a synergistic amount of a compound (B) according to claim 1 and at least one customary spot-on formulation adjuvant, and a notice specifying that the containers are to be used alternately with an interval.

71. A synergistic spot-on composition for the long lasting protection against fleas and ticks on mammals which comprises (a) a synergistic amount of fipronil and a synertistic amount of a compound which mimics juvenile hormones, and (b) at least one customary spot-on formulation adjuvant, wherein said adjuvant(s) includes an organic solvent having a dieletric constant of between 10 and 35.

72. The synergistic spot-on composition of claim 71, wherein said composition is a solution.

73. The synergistic spot-on composition of claim 71, wherein the compound which mimics juvenile hormones is selected from the group consisting of azadirachtin, diofenolan, fenoxycarb, hydroprene, kinoprene, methoprene, pyriproxyfen, tetrahydroazadirachtin and 4-chloro-2-(2-chloro-2-methyl-propyl)-5-(6-iodo-3-pyridylmethoxy)pyridizine-3(2H)-one.

74. The synergistic spot-on composition of claim 71, wherein the compound which mimics juvenile hormones is methoprene.

75. The synergistic spot-on composition of claim 71, 72, 73 or 74, wherein said solvent is selected from the group consisting of acetone, acetonitrile, benzyl alcohol, butyldiglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, diethylene glycol monoethyl ether, ethylene glycol, diethyl phthalate, and a mixture of at least two of these solvents.

76. The synergistic spot-on composition of claim 71, 72, 73 or 74, wherein said solvent is selected from the group consisting of butyldiglycol, dipropylene glycol n-butyl ether, ethylene glycol monoethyl ether, ethylene glycol monomethyl ether, dipropylene glycol monomethyl ether, liquid polyoxyethylene glycols, propylene glycol, diethylene glycol monoethyl ether, ethylene glycol, and a mixture of at least two of these solvents.

77. The synergistic spot-on composition of claim 71, 72, 73 or 74, wherein said solvent is diethylene glycol monoethyl ether.

78. The synergistic spot-on composition of claim 71, 72, 73 or 74, wherein said at least one adjuvant further includes a crystallization inhibitor, which is present in a proportion of from 1 to 20% (W/V).

79. The synergistic spot-on composition of claim 78, wherein said crystallization inhibitor is selected from the group consisting of:

polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, methacrylates and other acrylic derivatives, anionic surfactants, cationic surfactants, amine salts of formula $N^+R'R''R'''$ in which the radicals R are optionally hydroxylated hydrocarbon radicals;

nonionic surfactants;

amphoteric sufactants; and a mixture of at least two of these crystallization inhibitors.

80. The synergistic spot-on composition of claim 79, wherein said crystallization inhibitor is selected from the group consisting of various grades of polyvinylpyrrolidone, polyvinyl alcohols, copolymers of vinyl acetate and vinyl pyrrolidinone, polyoxyethylenated sorbitan esters, and various grades of polysorbate; and a mixture of at least two of these crystallization inhibitors.

81. The synergistic spot-on composition of claim 79, wherein said crystallization inhibitor is a mixture of polyvinylpyrrolidone, polyoxyethylenated sorbitan esters and/or various grades of polysorbates.

82. The synergistic spot-on composition of claim 71, 72, 73 or 74, further comprising a cosolvent having a dielectric constant of between 10 and 40, which is miscible with water and/or with said organic solvent.

83. The synergistic spot-on composition of claim 82, wherein said cosolvent has a boiling point below 100° C.

84. The synergistic spot-on composition of claim 82, wherein said cosolvent is selected from the group consisting of absolute ethanol, isopropanol and methanol.

85. The synergistic spot-on composition of claim 84, wherein said cosolvent is absolute ethanol.

86. The synergistic spot-on composition of claim 1, 5, 71, 72, 73 or 74, wherein said fipronil and said compound which mimics juvenile hormones are present in a ratio of about 1:1 to about 1:4.

87. The synergistic spot-on composition of claim 1, 5, 71, 72, 73 or 74, wherein said fipronil and said compound which mimics juvenile hormones are present in a ratio of about 1:1.

88. The synergistic spot-on composition of claim 1, 5, 71, 72, 73 or 74, wherein said fipronil is present from 1 to 20% W/V and said compound which mimics juvenile hormones is present from 1 to 20% W/V.

89. A synergistic spot-on composition comprising, a synergistic amount of fipronil, a synergistic amount of methoprene, wherein said fipronil and methoprene are present in a ratio of about 1:1, diethylene glycol monoethyl ether, absolute ethanol, polyvinylpyrrolidone, and polysorbate 80, wherein said composition is a solution.

90. A dosage form comprising from about 0.3 to 3 ml of said composition of claim 1, 5, 71, 72, 73, 74 or 89.

91. A dosage form comprising from about 0.3 to 1 ml of said composition of claim 1, 5, 71, 72, 73, 74 or 89.

92. A package comprising from about 0.3 to 3 ml of said composition of claim 1, 5, 71, 72, 73, 74 or 89.

93. A package comprising from about 0.1 to 3 ml of said composition of claim 1, 5, 71, 72, 73, 74 or 89.

94. The method of claim 49 or 69, wherein said composition is a solution.

95. The method of claim 94, wherein the composition is applied to a zone with a surface area of less than 10 $cm^2$.

96. The method of claim 94, wherein the composition is applied at two points between the animal's shoulders.

97. The method of claim 94, wherein the volume of said composition is from about 0.3 to 3 ml.

98. The method of claim 94, wherein the volume of said composition is from about 0.3 to 1 ml.

99. The method of claim 94, wherein the amount of said composition is from 0.1 to 40 mg/kg of fipronil and from 0.1 to 40 mg/kg of a compound which mimics juvenile hormones.

100. The method of claim 94, wherein said compound that mimics juvenile hormones is methoprene.

101. A method for controlling fleas and ticks on mammals over a long duration of time which comprises locally applying to the skin of said mammal the composition of claim 71, 72, 73, 74 or 89.

102. The method of claim 101, wherein the composition is applied to a zone with a surface area of less than 10 cm$^2$.

103. The method of claim 101, wherein the composition is applied at two points between the mammal's shoulders.

104. The method of claim 101, wherein the duration is two months.

105. The method of claim 101, wherein the duration is three months.

106. The method of claim 101, wherein said mammals are selected from the group consisting of cats and dogs.

107. The method of claim 101, wherein the volume of said composition is from about 0.3 to 3 ml.

108. The method of claims 101, wherein the volume of said composition is from about 0.3 to 1 ml.

* * * * *